(12) United States Patent
Beyerlein et al.

(10) Patent No.: US 7,425,096 B2
(45) Date of Patent: Sep. 16, 2008

(54) GANTRY FOR AN X-RAY DEVICE

(75) Inventors: Walter Beyerlein, Bubenreuth (DE); Werner Kühnel, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/632,573

(22) PCT Filed: Jul. 15, 2005

(86) PCT No.: PCT/EP2005/053413

§ 371 (c)(1),
(2), (4) Date: Jan. 16, 2007

(87) PCT Pub. No.: WO2006/008274

PCT Pub. Date: Jan. 26, 2006

(65) Prior Publication Data

US 2008/0049904 A1    Feb. 28, 2008

(30) Foreign Application Priority Data

Jul. 22, 2004    (DE)    ........................ 10 2004 035 603

(51) Int. Cl.
*H01J 35/16*    (2006.01)
(52) U.S. Cl. ..................................... 378/203; 378/101

(58) Field of Classification Search ............... 378/101, 378/117, 203
See application file for complete search history.

(56) References Cited

U.S. PATENT DOCUMENTS

| 4,323,781 A | 4/1982 | Baumann et al. |
| 4,912,735 A | 3/1990 | Beer |
| 5,530,422 A | 6/1996 | Harrison |
| 5,608,771 A | 3/1997 | Steigerwald et al. |

FOREIGN PATENT DOCUMENTS

| DE | 28 55 379 A1 | 7/1980 |
| DE | 195 33 820 A1 | 3/1996 |

OTHER PUBLICATIONS

International Search Report dated Oct. 11, 2005.
International Preliminary Examination Report (with translation) dated Nov. 9, 2006.

*Primary Examiner*—Jurie Yun
(74) *Attorney, Agent, or Firm*—Brinks, Hofer, Gilson & Lione

(57) ABSTRACT

The invention relates to a gantry for an x-ray device. According to the invention at least one screening device used to reduce interactions with electromagnetic disturbance fields is provided for the at least one transmitter for the non-contact power or signal transmission between a stationary part and a rotatable part of the gantry.

19 Claims, 3 Drawing Sheets

GANTRY FOR AN X-RAY DEVICE

The present patent document is a 371 of PCT Application Serial Number PCT/EP2005/053413, filed Jul. 15, 2005, designating the United States, which is hereby incorporated by reference. This application also claims the benefit of DE 10 2004 035 603.3, filed Jul. 22, 2004, which is hereby incorporated by reference.

BACKGROUND

The present embodiments relate to a gantry for an X-ray device.

In radiation therapy and in many computed tomography systems, signals are transmitted from a stationary part to a rotatable part of a gantry using a contactless transmitter for example, by induction. As a result, spark development and high wear in such transmission types as wiper rings are avoided. German Patent DE 28 55 379 C2 discloses a contactless power transmission.

As shown in FIG. 2, a contactless power transmitter for power transmission includes a primary coil on the stationary part of the gantry, a secondary coil on the rotatable part of the gantry, and at least one transmitter core. A plurality of transmitters for different system components to be supplied with power may also be present on one gantry.

For structural reasons, an air gap between the stationary part and the rotatable part of the gantry is unavoidable. A magnetic stray field develops around the air gap. The size of the magnetic stray field is in proportion to its size. The magnetic stray field of a transmitter can enter into interaction with the magnetic stray field of a different transmitter, with capacitive coupling paths for data transmission, or with electronic system components. The result of the interaction with other magnetic stray fields can be mutual interference with transmission, to the point of damage to system components.

If there are two transmitters side by side, of which the first is responsible for supply to the X-ray tube and the second is responsible for voltage supply otherwise, the interaction at the X-ray tube, despite the first transmitter having been switched off, can permanently cause a voltage of up to several kV. This can lead to unwanted radiation generation.

The interaction may possibly be reduced by creating a sufficient distance from the stray fields or between the stray fields. For example, for an air gap of approximately 1 mm, to attain any improvement the distance between two inductive transmitters would have to be at least 10 cm, but for structural reasons that is often not possible.

SUMMARY

The present embodiments may obviate one or more of the drawbacks or limitations of the related art. For example, in one embodiment, a simple and inexpensive way to reduce the effect on system components of magnetic stray fields that are caused for instance by the contactless inductive power transmission or other signal transmission, or by other electromagnetic interference fields, is provided.

In one embodiment, a gantry for an X-ray device is provided for receiving an X-ray tube and/or measurement value detection. A stationary part of the gantry is disposed in stationary fashion, and relative to the stationary part is a rotatable part of the gantry. The gantry is provided for receiving at least one transmitter for power transmission and/or signal transmission between the stationary part and the rotatable part. The power transmission and/or signal transmission between the stationary part and the rotatable part is provided in contactless fashion, in particular inductively and/or capacitively. At least one shielding device for the at least one transmitter is provided for shielding against electromagnetic interference fields.

In one embodiment, not only protection of the particular transmitter against electromagnetic interference fields from other transmitters or from external interference fields but also protection of other equipment components against the electromagnetic interference fields of that particular transmitter are assured using a shielding device for the at least one transmitter.

In one embodiment, at least one shielding device for the at least one transmitter is provided. The at least one shielding device shields against electromagnetic interference fields that occur as a result of the contactless power transmission and/or signal transmission. To enable assuring comprehensive mutual protection of at least two transmitters, expediently at least one shielding device for at least one transmitter is provided for shielding against electromagnetic interference fields, occurring as a result of the contactless power transmission and/or signal transmission, of the other transmitter or transmitters, respectively.

In one embodiment, at least one annular transmitter is provided. In this embodiment, the shielding device is formed by at least one annular shield element that is concentric with the respective transmitter. In this embodiment, the shielding device can be mounted at little expense and does not hinder the operation of the equipment. In one embodiment, at least one annular transmitter is provided. The shielding device is formed by at least one stationary annular shield element that is concentric to the stationary part of the respective transmitter and at least one rotatable annular shield element that is concentric with the rotatable part of the respective transmitter.

DETAILED DESCRIPTION

Figure 1:
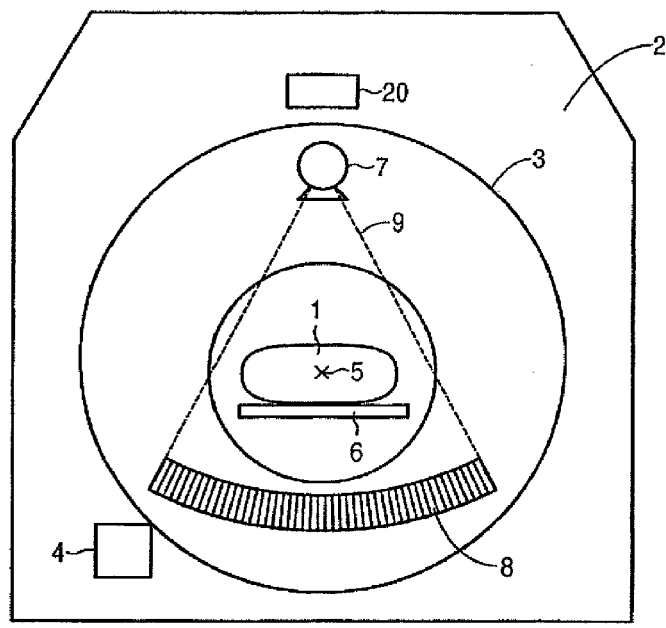
FIG. 1 shows a front view of an X-ray device with a gantry according to the prior art.

As shown in FIG. 1, an X-ray diagnosis device produces transverse slice images of a patient 1. One such system is known as a computed tomography system. The device has a gantry 3 provided in a frame 2. The gantry 3 has one part that is rotatable by a motor 4 about an axis 5 that extends perpendicular to the plane of the drawing. The gantry 3 includes an X-ray tube 7 and a detector 8 for X-raying the patient lying on a support 6.

the X-ray tube 7 emits a fan-shaped X-ray beam 9. The size of the X-ray beam 9 is selected such that the entire transverse slice to be examined of the patient 1 is penetrated by X-radiation. Perpendicular to the plane of the slice, the thickness of the X-ray beam 9 is equal to the slice thickness. For X-raying the patient 1, the assembly comprising the X-ray tube 7 and the detector 8 is rotated about the patient 1 by an angle of approximately 360°. A set of output signals of the detector 8 is called up at predetermined projections, for example, at each degree of angle.

The high voltage to the X-ray tube 7 from an X-ray generator 20 is transmitted in contactless fashion. Contactless signal transmission allows the measurement assembly 7, 8 to rotate constantly and have very short scanning times. Contactless signal transmission can be from a rotating part to a fixed part, for example, also inductively or via a stationary ring, curved around the pivot axis 5, of fiber optical material in a manner not described in further detail.

Figure 2:
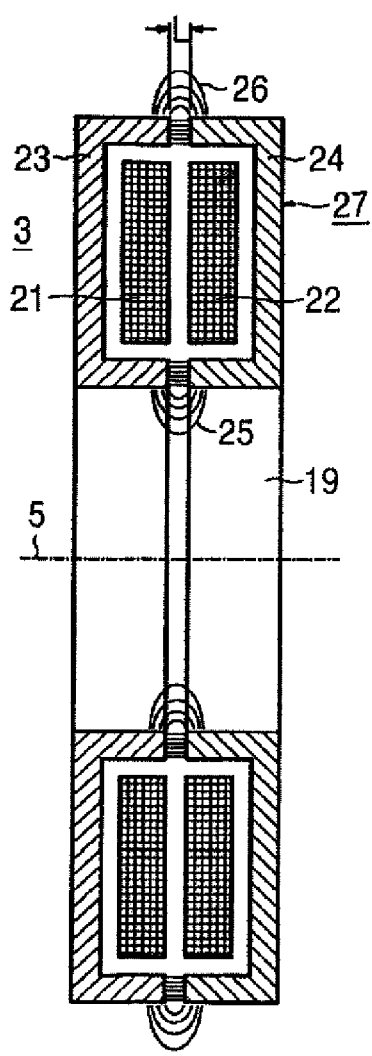
FIG. 2 shows a side view of a section through a gantry with an inductive power transmitter according to the prior art.

As shown in FIG. 2, a gantry 3 of the related art includes a single inductive transmitter 27. The transmitter 27 is disposed annularly around the opening 19 that serves to receive an object 1 and has a pivot axis 5. The stationary part of the transmitter 27 includes a primary coil 21 and a U-shaped transmitter core part 23. The rotatable part of the transmitter 27 includes a secondary coil 22 and a U-shaped transmitter core part 24. For structural reasons, there is an air gap L between the stationary part and the rotatable part of the transmitter 27. Magnetic stray fields 25 and 26 form around the air gap in both the inner and outer peripheral regions of the transmitter 27. The magnetic stray field 25 extends into the opening 19.

Figure 3:
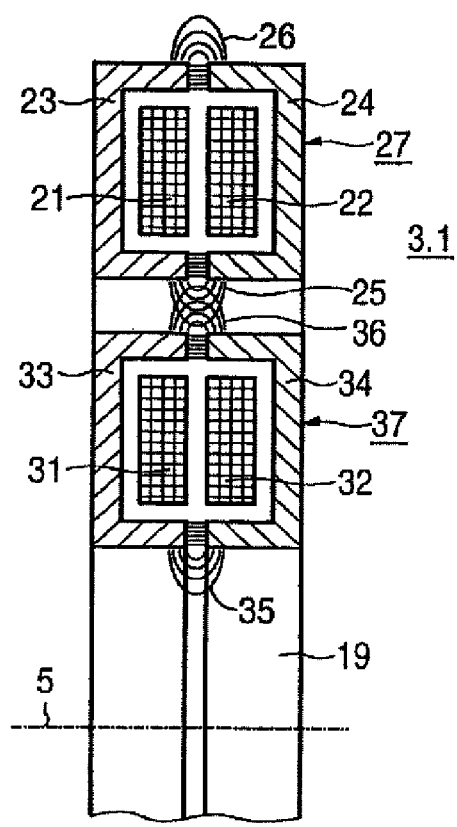
FIG. 3 shows a side view of a section through a gantry with two inductive power transmitters according to the prior art.

FIG. 3 shows a scanning unit as in FIG. 2, with two transmitters 27 and 37 of different radii. Each transmitter has one stationary part, with primary coils 21 and 31 as well as U-shaped transmitter core parts 23 and 33, and one rotatable part, with secondary coils 22 and 32 and U-shaped transmitter core parts 24 and 34. Magnetic stray fields 25, 26, 35 and 36 form in the region of the air gap L in both transmitters 27 and 37. The outward-oriented stray field 36 of the inner transmitter 37 and the inward-oriented stray field 25 of the outer transmitter 27 overlap, and the result can create wrong couplings.

Figure 4:
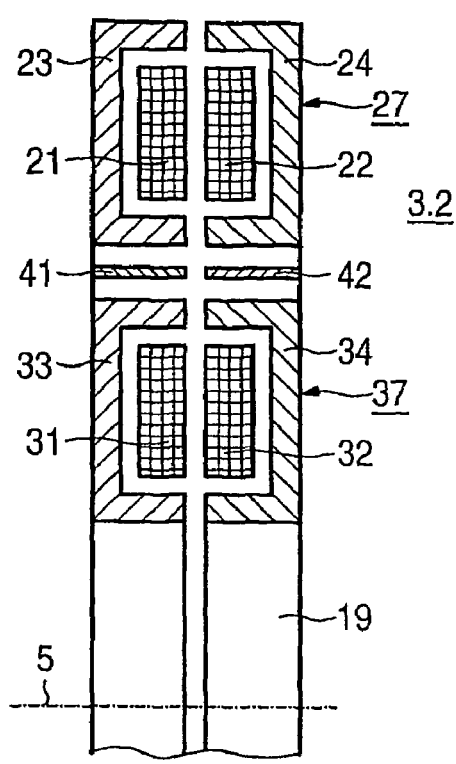
FIG. 4 shows a side view of one embodiment of a section through a gantry with two inductive power transmitters and shield elements.

As shown in FIG. 4, in one embodiment, a gantry 3.2 includes two annular transmitters 27 and 37 and annular shield elements 41 and 42. The annular shield elements 41 and 42 are disposed between the annular transmitters 27 and 37 to shield against the magnetic stray fields. The annular shield elements 41 and 42 are concentric to the respective transmitters 27 and 37 and can comprise different materials. In one embodiment, the annular shield elements 41, 42 are embodied as magnetostatic shielding, in particular of ferrite. Using materials such as ferrites that are poor electrical conductors, magnetic stray fields 25, 36, as shown in FIG. 3, can be statically shielded against. Using this type of shielding, no losses of electrical power occur.

The shield elements 41, 42 may also be constructed of different materials. In one embodiment, the annular shield elements 41, 42 are embodied for eddy current damping. In this embodiment, the annular shield elements 41, 42 include electrically conductive material, in particular iron. For the eddy current damping, it is appropriate for the shield elements to form a closed surface. The way the eddy current damping works is that the stray field induces eddy currents in the conductive shielding rings. This creates a contrary field, which acts counter to the original stray field and leads to its compensation. The eddy current damping can effectively shield against stray fields with even only very thin shield elements.

Figure 5:
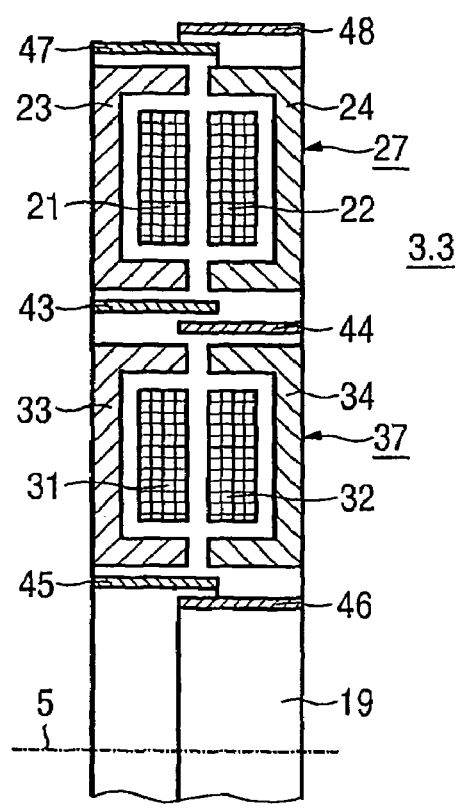
FIG. 5 shows a side view of one embodiment of a section through a gantry with two inductive power transmitters and overlapping shield elements.

As shown in FIG. 5, in one embodiment, a gantry 3.3 includes annular shield elements 43-48. At least partial mutual axial overlap (parallel to the pivot axis 5) of the shield elements 43-48 is provided for more than one of the annular shield elements 43-48. In one embodiment, at least one transmitter 27, 37 and one shielding device 47, 48 is provided outside the outer contour of the largest transmitter 27, and one shielding device 45, 46 is provided inside the inner contour of the smallest transmitter 37. In this embodiment, equipment components located outside and inside the gantry 3.3, and persons as well, are protected against the stray fields, and the tolerance levels permitted are adhered to. The transmitters are also protected against damaging electromagnetic stray fields.

Figure 6:
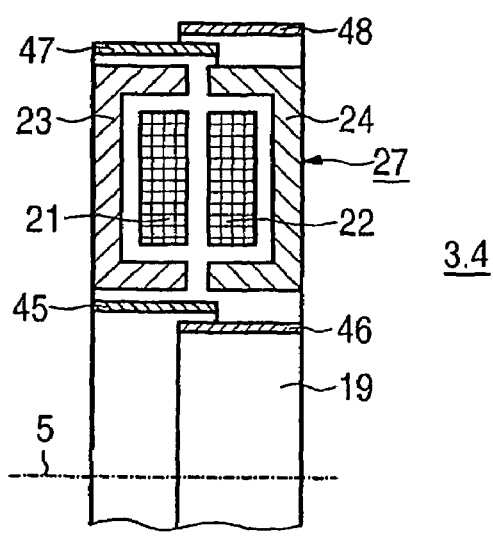
FIG. 6 shows a side view of one embodiment of a section through a gantry having an inductive power transmitter and shield elements.

As shown in FIG. 6, in one embodiment, a gantry 3.4 includes a single transmitter 27 and annular shield elements 45-48. The thickness of the shield elements 41-48 is oriented to the penetration depth of the induced currents and may be in the range of 1 mm, for example.

In one embodiment, a gantry for an X-ray device includes at least one transmitter for contactless power transmission and signal transmission between a stationary part and a rotatable part of the gantry, and at least one shielding device for reducing interactions with electromagnetic interference fields.

The invention claimed:

1. A gantry for an X-ray device, including:
   an X-ray tube and a detector;
   a stationary part disposed in stationary fashion;
   a rotatable part that is rotatably supported, the rotatable part being movable relative to the stationary part;
   at least one annular transmitter for power transmission and/or signal transmission disposed between the stationary part and the rotatable part;
   at least one shielding device that includes an annular shield element concentric with a respective one of the at least one annular transmitters and shields against electromagnetic interference fields; and
   contactless power transmission and/or signal transmission between the stationary part and the rotatable part, inductively and/or capacitively.

2. The gantry as defined by claim 1, wherein the at least one shielding device for the at least one transmitter is operable to shield against electromagnetic interference fields that occur as a result of the contactless power transmission and/or signal transmission.

3. The gantry as defined by claim 2, comprising at least two annular transmitters, the at least one shielding device for a first transmitter of the at least two annular transmitters is operable to shield against electromagnetic interference fields that occur as a result of the contactless power transmission and/or signal transmission of a second transmitter of the at least two annular transmitters.

4. The gantry as defined by claim 1, wherein the at least one shielding device is provided outside an outer contour of a transmitter that is a largest transmitter of the at least one annular transmitters.

5. The gantry as defined by claim 1, wherein the at least a first transmitter and at least a first shielding device are disposed inside an outer contour of a transmitter that is a largest transmitter of the at least one annular transmitters.

6. The gantry as defined by claim 1, wherein the at least one shielding device includes at least one stationary annular shield element that is concentric to the stationary part of the respective at least one transmitter and at least one rotatable annular shield element that is concentric with the rotatable part of the respective at least one transmitter.

7. The gantry as defined by claim 6, wherein the at least one shielding device includes another annular shield element that partly overlaps a mutual axis of the at least one stationary annular shield element.

8. The X-ray device as defined by claim 7, wherein the annular shield elements include magnetostatic shielding.

9. The gantry as defined by claim 8, wherein the annular shield elements comprise ferrite.

10. The gantry as defined by claim 6, wherein the annular shield elements include magnetostatic shielding.

11. The gantry as defined by claim 6, wherein the annular shield elements are embodied as an eddy current damping.

12. The gantry as defined by claim 11, wherein the annular shield elements comprise electrically conductive material.

13. The gantry as defined by claim 12, wherein the annular shield elements comprise iron.

14. The X-ray device as defined by claim 6, wherein the annular shield elements comprise ferrite.

15. An X-ray device comprising:
a gantry that includes an X-ray tube and a detector;
a stationary part disposed in stationary fashion;
a rotatable part that is rotatably supported, the rotatable part being movable relative to the stationary part;
at least one annular transmitter for power transmission and/or signal transmission disposed between the stationary part and the rotatable part;
at least one shielding device that includes an annular shield element concentric with a respective one of the at least one annular transmitters and shields against electromagnetic interference fields; and
contactless power transmission and/or signal transmission between the stationary part and the rotatable part inductively and/or capacitively.

16. The X-ray device as defined by claim 15, wherein the at least one shielding device is provided outside an outer contour of a transmitter that is a largest transmitter of the at least one annular transmitter.

17. The X-ray device as defined by claim 15, wherein at least a first transmitter and at least a first shielding device are disposed inside an outer contour of a transmitter that is a largest transmitter of the at least one annular transmitters.

18. The X-ray device as defined by claim 15, wherein the at least one shielding device includes at least one stationary annular shield element that is concentric to the stationary part of the respective at least one transmitter and at least one rotatable annular shield element that is concentric with the rotatable part of the respective at least one transmitter.

19. The X-ray device as defined by claim 18, wherein the at least one shielding device includes another annular shield element that partly overlaps a mutual axis of the at least one stationary annular shield element.

* * * * *